(12) United States Patent
Liu et al.

(10) Patent No.: US 10,937,137 B2
(45) Date of Patent: Mar. 2, 2021

(54) IMAGE CALIBRATION METHOD AND DETECTING DEVICE

(71) Applicant: Qisda Corporation, Taoyuan (TW)

(72) Inventors: Fang-Bin Liu, Hsinchu (TW); Chang-Te Lin, Toucheng Township (TW)

(73) Assignee: Qisda Corporation, Taoyuan (TW)

( * ) Notice: Subject to any disclaimer, the term of this patent is extended or adjusted under 35 U.S.C. 154(b) by 51 days.

(21) Appl. No.: 16/506,424

(22) Filed: Jul. 9, 2019

(65) Prior Publication Data

US 2020/0065951 A1 Feb. 27, 2020

(30) Foreign Application Priority Data

Aug. 23, 2018 (CN) .......................... 201810968210.8

(51) Int. Cl.
*G06K 9/00* (2006.01)
*G06T 5/50* (2006.01)
*A61B 8/08* (2006.01)
*A61B 8/00* (2006.01)
*G06T 7/80* (2017.01)

(52) U.S. Cl.
CPC .............. *G06T 5/50* (2013.01); *A61B 8/0841* (2013.01); *A61B 8/4444* (2013.01); *A61B 8/5207* (2013.01); *A61B 8/5215* (2013.01); *G06T 7/80* (2017.01); *G06T 2207/10132* (2013.01)

(58) Field of Classification Search
CPC .... G06T 5/50; G06T 2207/10132; G96T 7/80
See application file for complete search history.

(56) References Cited

U.S. PATENT DOCUMENTS 5,655,535 A * 8/1997 Friemel ................ A61B 8/0866
128/916
10,368,833 B2 * 8/2019 Patruno ................... A61B 8/14
(Continued)

FOREIGN PATENT DOCUMENTS

EP  3 255 607 A1  12/2017
EP  3255607 A1 * 12/2017 ............... G06T 7/10

OTHER PUBLICATIONS

A Novel Closed Form solution for Ultrasound Calibration., Emad M. Boctor et al., ResearchGate, Jan. 2004, pp. 527-530 (Year: 2004).*

*Primary Examiner* — Jayesh A Patel

(57) ABSTRACT

An image calibration method of the present invention is configured to calibrate the position of observation area in motion image which includes image frames. The step of the image calibration method includes: determining the observation area and acquires central position of the observation area in first image frame of the motion image; determining first unique area, which complies with gradient characteristic, in the first image frame; acquiring first vector value from the central positions of the observation area to the first unique area in the first image frame; finding second unique area in the second image frame of the motion image according to the gradient characteristic; acquiring second vector value from the central position of the observation area to the central position of the second unique area in the second image frame; and calibrating position of the observation area in a third image frame according to the difference between the first vector and the second vector.

14 Claims, 9 Drawing Sheets

(56) References Cited

U.S. PATENT DOCUMENTS

| | | | |
|---|---|---|---|
| 2010/0060644 A1* | 3/2010 | Elie | A61B 8/481 |
| | | | 345/440 |
| 2013/0116538 A1* | 5/2013 | Herzog | A61B 5/0035 |
| | | | 600/407 |
| 2013/0172739 A1* | 7/2013 | Paladini | A61B 6/5247 |
| | | | 600/436 |
| 2016/0098621 A1* | 4/2016 | Tahmasebi Maraghoosh | |
| | | | A61B 5/055 |
| | | | 600/411 |
| 2017/0103518 A1* | 4/2017 | Murphy | A61B 8/461 |
| 2019/0378239 A1* | 12/2019 | Zhu | G06T 1/20 |
| 2020/0306565 A1* | 10/2020 | Boyce | G06T 5/002 |

* cited by examiner

IMAGE CALIBRATION METHOD AND DETECTING DEVICE

FIELD OF THE INVENTION

The present invention relates to a calibration method and a detecting device, and more particularly, to a image calibration method and a detecting device for an ultrasound image.

BACKGROUND

Medical ultrasonography is a medical image diagnosis technique based on ultrasound images, displaying the sizes, structures, and sources of diseases of the muscles and the internal organs within human bodies. In the application of ultrasonography, Doppler ultrasound has increased the ability of medical ultrasonography greatly. The flow of fluid within human body or organism, such as direction and speed of blood flow, can all be detected by using Doppler ultrasound, and it is especially efficient in the cardiovascular related fields.

However, the observation area of Doppler ultrasound is selected mainly by the user according to the image generated by ultrasound. Tracking specific area within a continuous image has always been a subject of research. When watching the ultrasound images, the images may be interfered by the user's hand shakes, moves or presses when holding the ultrasound probe, the heartbeat, breath or movement of the subject itself. The observation area of Doppler ultrasound is located according to the image generated by ultrasound, thus the interference of the ultrasound image will influence the observation area of Doppler ultrasound, reducing the accuracy of the Doppler ultrasound.

SUMMARY

The invention provides an image calibration method which is configured to calibrate the position of an observation area in a motion image.

A detecting device of the present invention can improve the accuracy of its detection results.

The image calibration method of the present invention is configured to calibrate the position of an observation area in a motion image which includes image frames. The step of the image calibration method includes: determining the observation area of the motion image and acquires a central position of the observation area in a first image frame of the motion image; determining a first unique area, which complies with a gradient characteristic, in the first image frame of the motion image; acquiring a first vector pointing from the central position of the observation area to a central position of the first unique area in the first image frame; determining a second unique area in the second image frame of the motion image according to the gradient characteristic; acquiring a second vector pointing from the central position of the observation area to a central position of the second unique area in the second image frame; and calibrating position of the observation area in a third image frame according to the difference between the first vector and the second vector.

In an example of the present invention, the step of determining the first unique area includes determining a contour image of the first image frame and determining the first unique area from the contour image. The pixels of the partial contour image of the first unique area contains the same connected-component labeling, and the step further includes acquiring the gradient characteristic from the partial first image frame corresponded to first unique area.

In an example of the present invention, the step of determining the contour image includes: acquiring an open image and a close image of the first image frame. The open image is an image of the first image frame which has been through the erosion then the dilation of morphology in digital image processing techniques, and the close image is an image of the first image frame which has been through the dilation then the erosion. The contour is determined with the absolute value of the difference between the open image and the close image.

In an example of the present invention, the step of determining the first unique area further includes: dividing the contour image into various pixel groups according to connected-component and determining a pixel group with the largest number of pixels among the pixel groups as the first unique area.

In an example of the present invention, the step of acquiring the gradient characteristic further includes determining the gray-level co-occurrence matrix (GLCM) of the partial first image frame in the unique area as gradient characteristic.

In an example of the present invention, the step of determining the unique area further includes: dividing the first image frame into various sub-images; and determining the first unique area in each sub-image. The following image frame then, as the first image frame, is divided into various sub-images and finds unique area respectively in each sub-image according to the gradient characteristic.

In an example of the present invention, the motion image is ultrasound image, after the user determining the observation area in the image frame of the motion image further includes: acquiring Doppler signal of the partial image frame in the observation area.

The detecting device of the present invention is used to detect an organism. The detecting device includes image capturing device, processor, displayer and input device. The image capturing device captures motion image which includes image frames from the organism. The processor connects to the image capturing device and acquires motion image from the image capturing device. The displayer connects to the processor and displays the motion image from the processor. The input device connects to the processor and determines an observation area from the first image frame of the motion image.

The processor acquires the central position of the observation area after determining the observation area, determines a first unique area in the first image frame which complies with a gradient characteristic, acquires a first vector value from the central position of the observation area to the central position of the first unique area, finds a second unique area in a second image frame according to the gradient characteristic in the motion image, acquires a second vector value from the central position of the observation area to the central position of the second unique area in the second image frame, and calibrates the position of the observation area in a third image frame according to the difference between the first vector and the second vector.

In an example of the present invention, the processor determines a contour image of the first image frame, and the first unique area is determined from the contour image. The pixel of the partial contour image in the first unique area contains the same connected-component labeling. The processor acquires the gradient characteristic from the partial first image frame corresponded to the first unique area.

In an example of the present invention, the processor acquires an open image and a close image of the first image frame. The open image is the image which has been through the erosion then the dilation of morphology in digital image processing techniques, and the close image is the image of the image frame which has been through the dilation then the erosion. The absolute value of the difference between the open image and the close image determines the contour image.

In an example of the present invention, the processor divides the contour image into various pixel groups according to connected-component and determines the pixel group with the largest number of pixels among the pixel groups as the first unique area.

In an example of the present invention, the processor divides the contour image into various sub-images and determines the first unique area in each sub-image. The processor corresponded to the first image frame divides the second image frame into various sub-images and finds the second unique area in each sub-image of the second image frame according to the gradient characteristic.

In an example of the presented invention, the processor determines the gray-level co-occurrence matrix (GLCM) of the partial first image frame in the first unique area as the gradient characteristic.

In an example of the present invention, the image capturing device includes an ultrasound probe, and after the user determining the observation area from the first image frame in the motion image via the input device, the processor acquires the corresponding Doppler signal of the partial image frame in the observation area from the ultrasound probe.

In conclusion, by tracking the position of the unique area of each image frame in the motion image according to the gradient characteristic, the image calibration method of the present invention is configured to calibrate the position of observation area in each image frame effectively, and the detecting device of the present invention can also provide accurate detection results from the calibrated observation area in the image frame.

DETAILED DESCRIPTION OF THE PREFERRED EMBODIMENT

The detecting device and the configured image calibration method of the present invention can be applied to detecting devices that provide images, the preferred devices would be those provide medical images of organism. For instance, the detecting devices such as ultrasound devices which are suitable for providing real time medical images of organism, but the present invention is not limited thereto. Any personnel having ordinary skill in the art can apply the detecting device and the configured image calibration method to other organism and medical image devices, the preferred would be the detecting device which requires to select specific observation area in the image provided by the detecting device. The following will take ultrasound device as instance to elaborate, but this is not used to limit the present invention.

Figure 1:
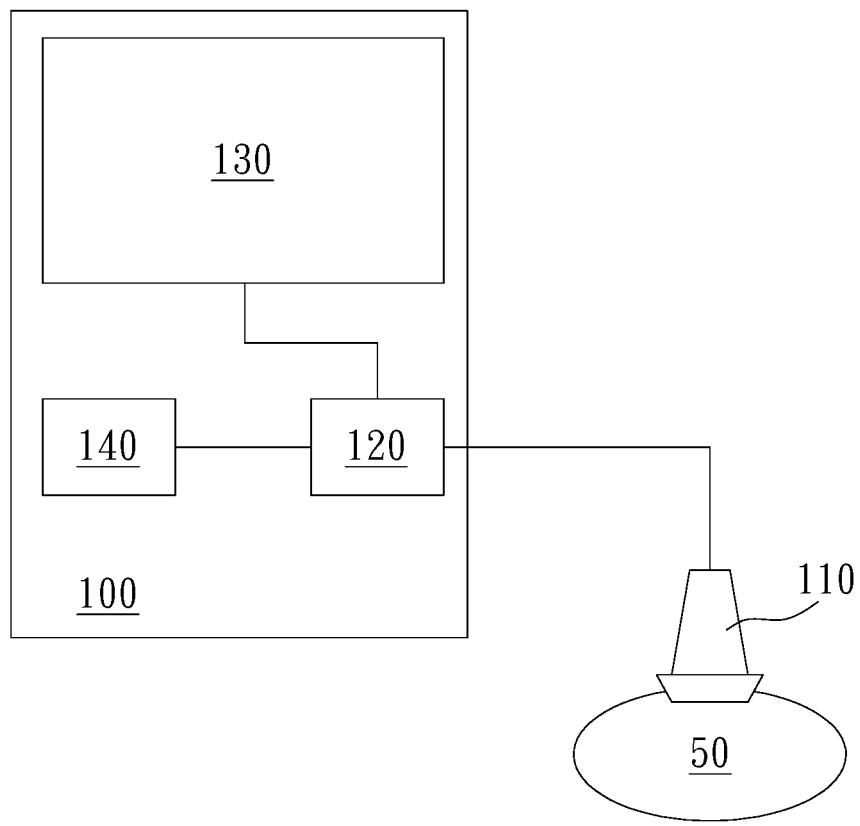
FIG. 1 is a schematic view of the detecting device of the present invention.

FIG. 1 is the schematic view of the detecting device in an embodiment of the present invention. Please refer to FIG. 1, in the embodiment of the present invention, the detecting device 100 includes image capturing device 110, processor 120, displayer 130 and input device 140, wherein the processor 120 connects to the image capturing device 110, displayer 130 and input device 140. The detecting device 100 is adapted to detect images of organism 50, and a motion image of the organism 50 is acquired via image capturing device 110 and displayed on the displayer 130.

More specifically, the image capturing device 110 of the example can emit detecting signals towards the organism 50 and generates a correspondent motion image by receiving the detecting signals reflected from or penetrated through the organism 50 or by receiving signals from the outside. In other words, the present invention is not limited to the method of acquiring the motion image from the organism 50 via image capturing device 110.

The following will take ultrasound as an instance to elaborate further. The detecting device 100, for instance, is an ultrasound detecting device; the image capturing device 110 is, for instance, an ultrasonic transducer or an ultrasonic sensor, used to detecting the organism 50 and acquiring a motion image. The motion image is formed by image frames which are two-dimension ultrasound images: the better ultrasound images would be acquired under brightness mode (B-mode), and these ultrasound images respectively become the image frames to form the motion image.

The processor 120 in the example can acquire the motion image from the image capturing device 110, allowing the detecting device to display the motion image and send out input instruction. To be more precise, the processor 120 is, for instance, the central processing unit (CPU) of the detecting device 100, it can also be the CPU within the computer device connected to the detecting device 100, but the present invention is not limited to this.

The processor 120 of the example connects to the displayer 130. The detecting device 100 can display via the displayer 130 the motion image acquired from the image capturing device 110 by the processor 120. The displayer 130 is, for instance, a liquid crystal display (LCD) used to display the motion image from the image capturing device 110, but the present invention is not limited to the type of the displayer 130.

The input device 140 connecting to the processor 120 is used to receive the instruction of the users such as doctors, examiners, operators and etc. The input device 140 of the example includes, for instance, keyboard, joystick, trackball, mouse, or even a touch module configured in the displayer 130. In the example, the user can give instructions via the input device 140 according to the motion image displayed by the displayer 130, for instance, determining a position of observation area in the motion image via input device 140.

The following will refer to the aforementioned detecting device 100 and the component labels as a whole to further elaborate the detecting device 100 and the image calibration method of the present invention. It should be understandable that, although the terms such as "the first," "the second" and etc. in this document can be used to describe different components, area or image, these components, areas and images should not be limited to these terms. These terms are used merely to separate one component, area or image from the other. Therefore, in the following discussion, the first component, area and image can be called the second component, area and image without departing from the teaching of this document.

Figure 2:
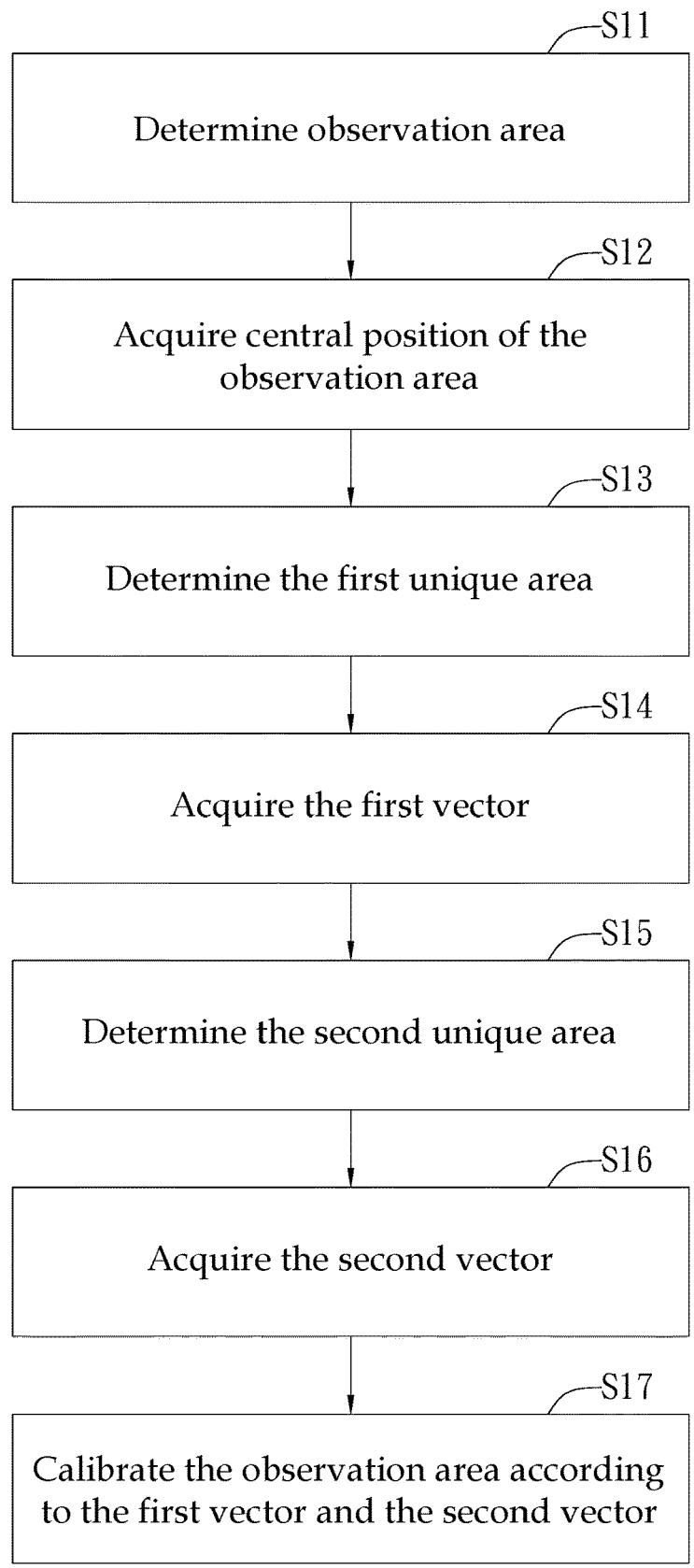
FIG. 2 is a flow chart of the image calibration method of the present invention.

FIG. 2 is the flow chart of image calibration method in an example of the present invention. Please refer to FIG. 2, the image calibration method of the example first determines the observation area in the first image frame of the motion image (Step S11). The first image frame here can be any of the image frames of the motion image, the preferred would be the image frame selected to determine the observation area when the user is operating the image capturing device 100.

In order to explain explicitly the image calibration method of the present invention, the following will use the simplified schematic view of image to elaborate the detecting device and the image calibration method of the present invention, but this is not used to limit the present invention. Please first refer to FIG. 2, after the user determining the observation area in the first image frame (Step S11), the image calibration method of the example acquires a central position of the observation area in the first image frame (Step S12).

After acquiring the center of the observation area, the image calibration method of the example then determines a first unique area and its gradient characteristic in the first image frame (Step S13). The gradient characteristic contains related information of the gradient of the image, the related information includes distribution direction, adjacent gap, brightness variation, and the processor 120 can find the position of the first unique area in other image frame of the motion image according the gradient characteristic. For instance, the first unique area can be an area with greater variation of gradient intensity than a variation of the gradient intensity in other part of the first image frame. The first unique area might be tissue such as muscles which can be a positioning target.

After finding the first unique area and gradient characteristic (Step S13), the image calibration method of the example acquires the first vector (Step S14). The first vector is related to the relative distance and direction between the central positions of the observation area and the first unique area: for instance, the vector in the example represents a direct displacement from the central position of the observation area of the observation area to a central position of the first unique area, but the invention is not limited thereto.

After acquiring the first vector, the first unique area and the gradient characteristic of the first unique area, the image calibration method of the example then determines the second unique area in the second image frame according to the gradient characteristic (Step S15). The second image frame is, for instance, the image frame acquired after the image capturing device 110 acquiring the first image frame, the processor 120 determines the second unique area in the second image frame according to the gradient characteristic, that is, finding the corresponding area in the second image frame according to the gradient characteristic acquired in the first unique area.

The image calibration method of the example acquires the second vector according to the second unique area and the observation area (Step S16). In the example, when the processor 120 determines the second unique area according to the gradient characteristic, the position of the observation area in the first image frame is as the same as in the second image frame, the second vector is the relative distance and direction between the central positions of the observation area and the second unique area: in the example, the central position of the observation area to the second unique area is determined to be the second vector, but the invention is not limited thereto.

The image calibration method of the example compares the first and the second vectors after acquiring the second vector. The image calibration method of the example acquires a difference between the second and the first vectors and calibrates the observation area accordingly (Step S17). By using the second vector acquired in the second image frame and the first vector acquired in the first image frame, the image calibration method of the example can calibrate the position of the observation area in the next image frame (i.e. the third image frame) with the difference of the second and the first vector. The image calibration method of the example calibrates the position of the observation area according to the position variation in each image frame of the unique area in the motion image, so as to provide fine calibrated results. For instance, when the image capturing device 110 is an ultrasound probe and the observation area is the area where the user captures the Doppler signal, the detecting device 100 can provide the accurate Doppler ultrasound signal by using the image calibration method. The invention does not limit to using the difference between the second and the first vector to calibrate to the position of the observation area in the third image frame; in other examples, the position of the observation area in the second image frame can even be calibrated promptly by the difference of the second and the first vector, but the invention is not limited thereto, it all depends on the process ability of the detecting device 100 and accuracy requirement of the calibration. The following will use the schematic view of the image frames again to elaborate specifically the image calibration method and the detecting device of the present invention.

FIG. 3A to 3D is the schematic view of the image frame in the first example of the present invention, to explain more explicitly, the black or dark areas in the image frame in the schema are hatched, wherein the coloring is not intended to limit the present invention. Please refer to the schematic view of the image frame in FIG. 3A, the following will refer to component labels of the detecting device 100 above as a whole to elaborate explicitly the image calibration method and the detecting device, wherein after the observation area A1 is determined by the user via input device 140, the processor 120 acquires the central position X1 of the observation area A1, that is, the position of the center X1 of the observation area A1 in the first image frame F1. Take B-mode ultrasound image and Doppler ultrasound as examples, the observation area A1 is, for instance, the area where the user selected to be detected by the Doppler ultrasound, so as to observe the blood speed and flow direction in observation area C.

After the user selecting the observation area A1 in the first image frame F1 via input device 140, the processor 120 acquires the position X1 of the observation area A1 in the first image frame. Then, the processor 120 determines the first unique area B1 in the first image frame F1, acquiring the gradient characteristic of the first unique area B1. The gradient characteristic, for example, is that the first unique area B1 has a greater variation of gradient intensity than the gradient intensity in other part of the first image frame. The processor 120 determines the displacement from the central position X1 of the observation area A1 to the central position X2 of the first unique area B1 as the first vector V1.

Figure 3A:
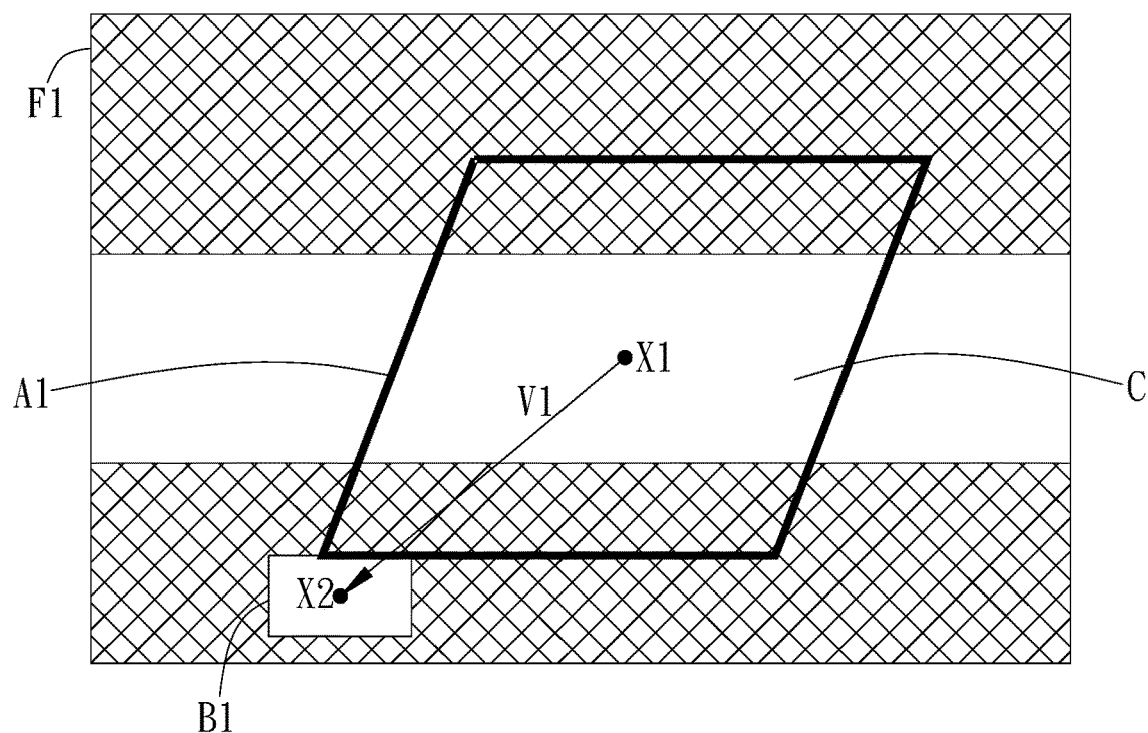
FIG. 3A to 3D are schematic views of image frames during the image calibration method of the first embodiment of the present invention.
Figure 3B:
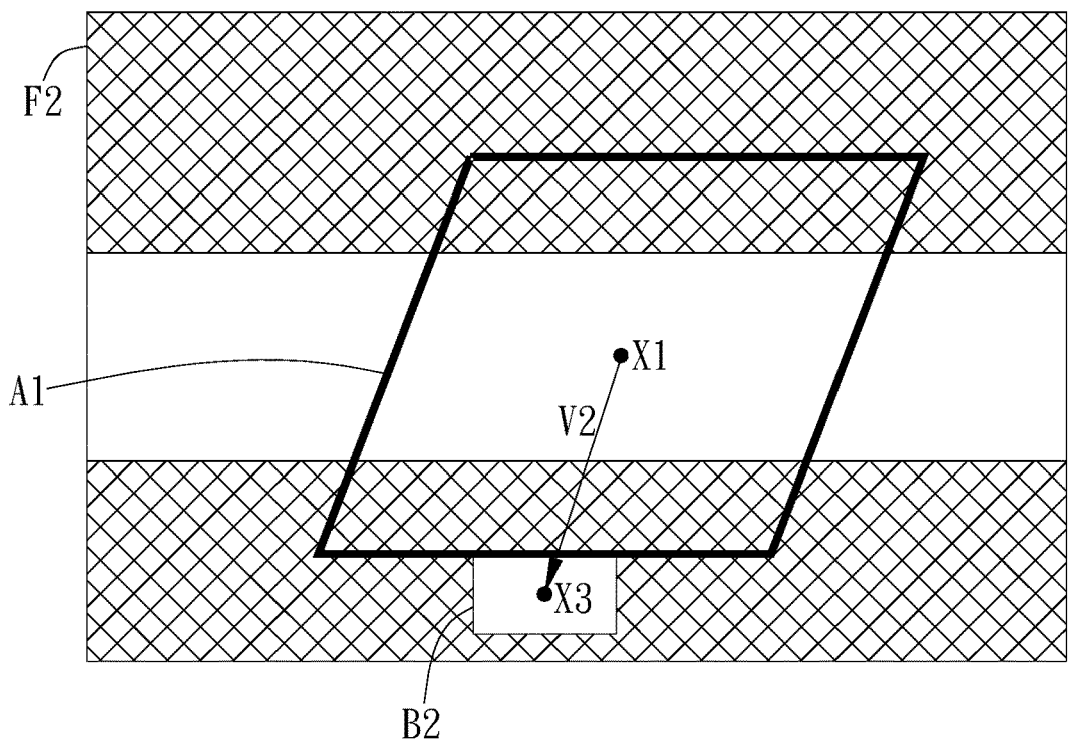

Please refer to FIG. 3B, after acquiring the first vector V1, due to the displacement when the user holding the detecting device, the second unique area B2 and the second vector V2 is acquired in the second image frame F2. To be precise, a while after the processor 120 acquiring the first vector V1, the second image frame F2 is acquired by the image capturing device 110, and the second unique area B2 is found in the second image frame F2 according to the gradient characteristic of the first unique area B1. The processor 120 determines the second vector V2 from the central position X1 of the observation area A1 to the central position X3 of the second unique area B2.

Figure 3C:
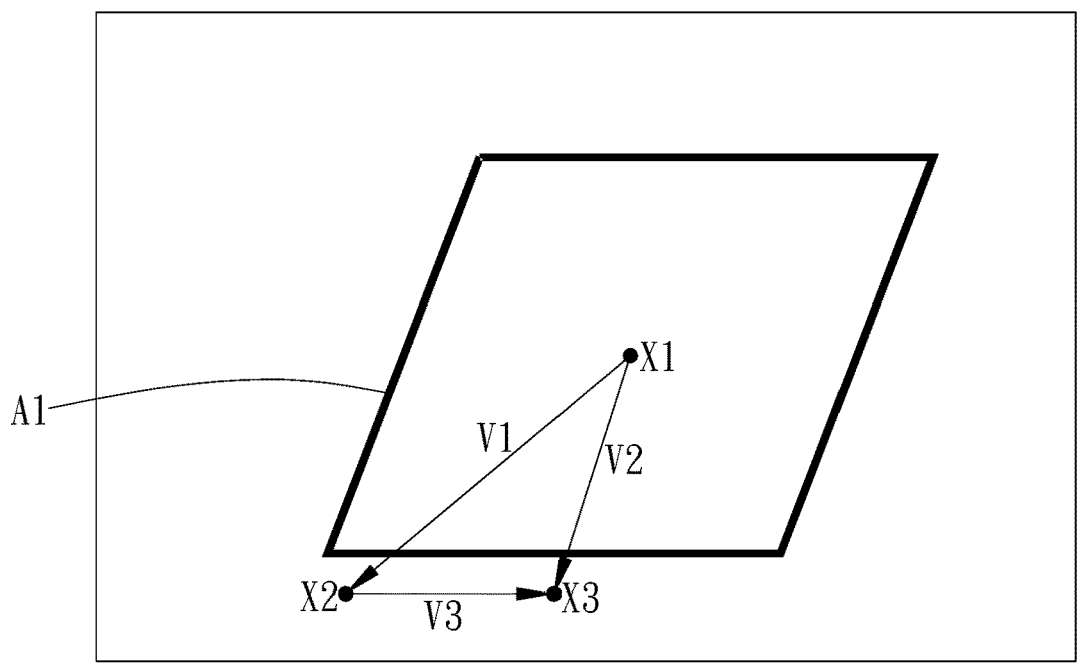

Please refer to FIG. 3C, after acquiring the first vector V1 and the second vector V2, the calibration vector V3 is determined according to the difference between the second vector V2 and the first vector V1. After acquiring the first vector V1 and the second vector V2 related to the central position X1 of observation area A, the processor 120 acquires the calibration vector V3 by calculating their difference and provides a calibration instruction according to the calibration vector V3.

Figure 3D:
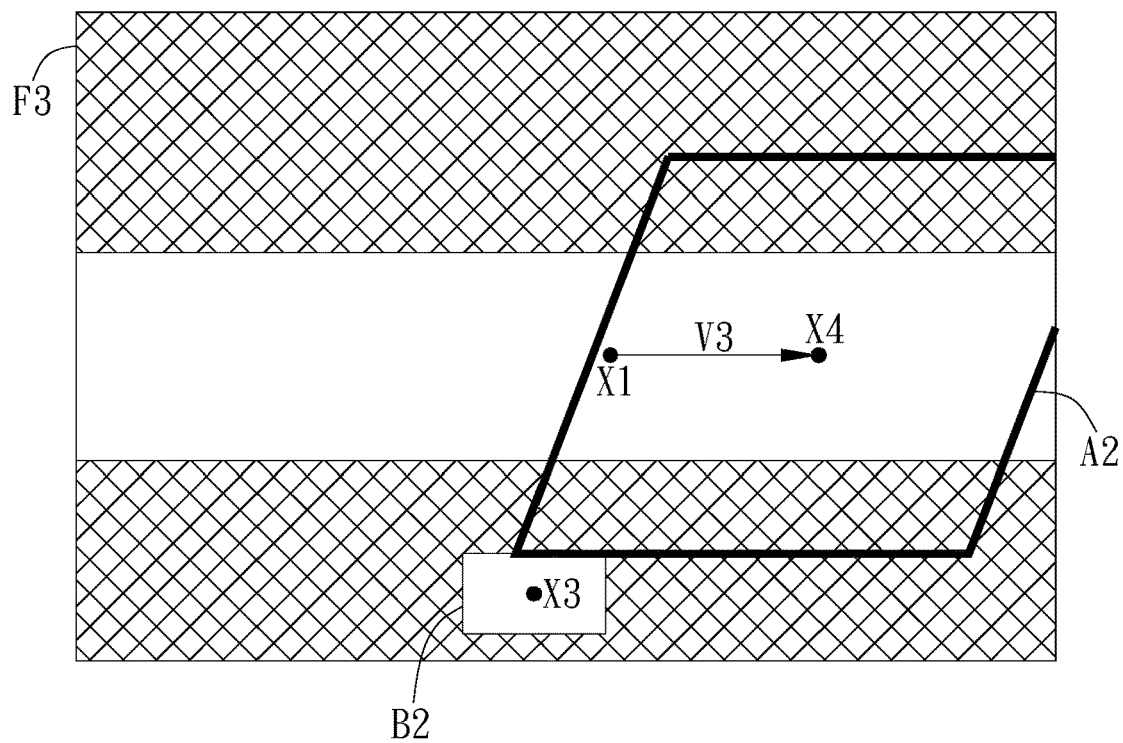

Please refer FIG. 3D, in the third image frame F3, the observation area A2 can calibrate calibration vector V3. To be more specific, when the processor 120 acquires the calibration vector V3, the processor 120 can calibrate the position of the observation area A1 according to the calibration vector V3 and calibrate the observation area A1 to the observation area A2. Since the calibration vector V3 is produced according to the unique area in the image frame, by using the image calibration method of the example, the observation area can be kept in the observing area as the user wishes so as to provide fine detecting results.

Figure 4:
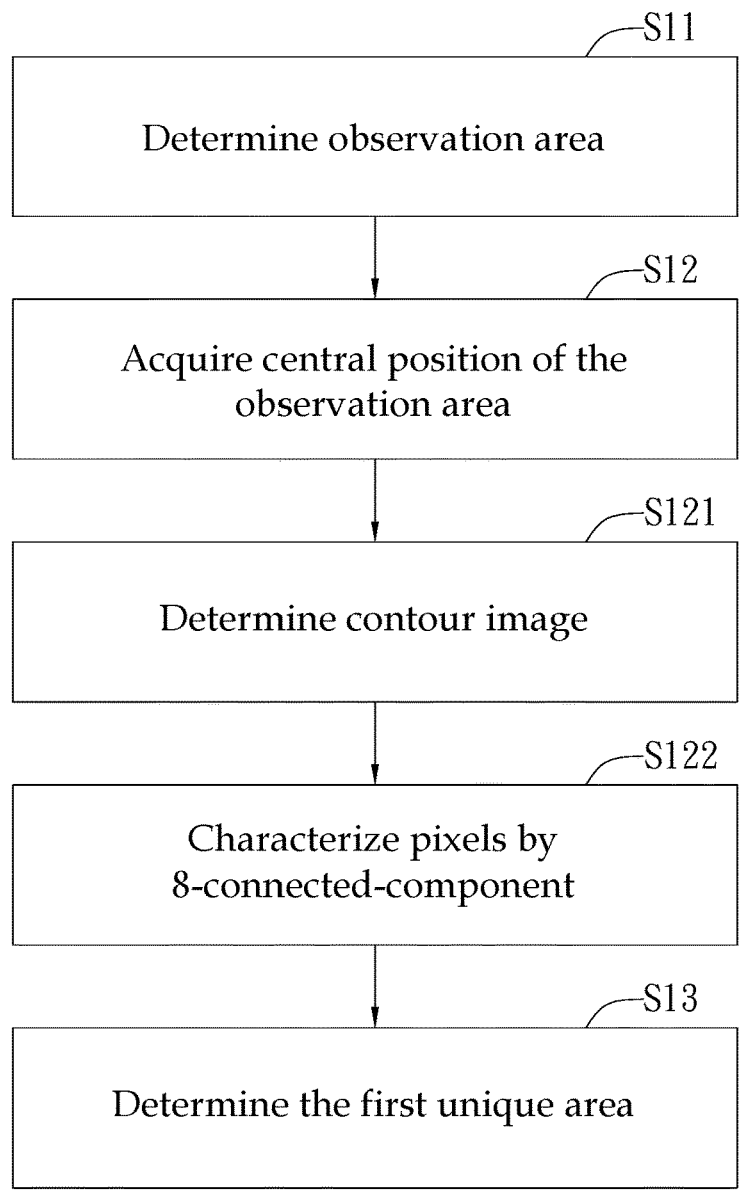
FIG. 4 is a flow chart of the image calibration method determine the first unique area of the present invention.

Furthermore, the image calibration method of the present invention can also determine the first unique area by the contour image. FIG. 4 is the flow chart of the process of determining the first unique area by using the image calibration method in an example of the present invention. Please refer to FIG. 4, in the image calibration method of the example, after determining the observation area (Step S11), the user acquires the central position of the observation area (Step S12). After acquiring the central position of the observation area (Step S12), the image calibration method of the example determines a contour image from the first image frame (Step S121). To be more precise, the image calibration method takes the area with greatest pixel variation as the unique area and selects the area with greater gradient variation according to gradient morphology. In terms of mathematical morphology, the image calibration method of the example finds the outline in the first image frame, that is, finding a contour image of each pattern in the first image frame so as to form a contour image.

After acquiring the contour image of the first image frame, the image calibration method of the example characterized the pixel in the image by connected-component (Step S122). Since the image calibration method of the example acquires the contour image in the image according to gradient morphology, the contour image can be divided into various sections by using the connected-component such as 8-connected-components, then regard the biggest section as the first unique area (Step S13). More precisely, after 8-connected-components characterized the contour image (Step S12), the contour image will contain various connected-components labeling, and the biggest section with the same connected-component labeling among the pixels will be determined as the first unique area. After dividing the contour image by 8-connected-component, the area with the largest number of pixels is the first unique area. 8-connected-component is used as an instance in the example; in other examples, the pixel in the image frame can even be characterized by 4-connected-component or other connected-component with different quantities or shapes, the present invention is not limited thereto.

Figure 5:
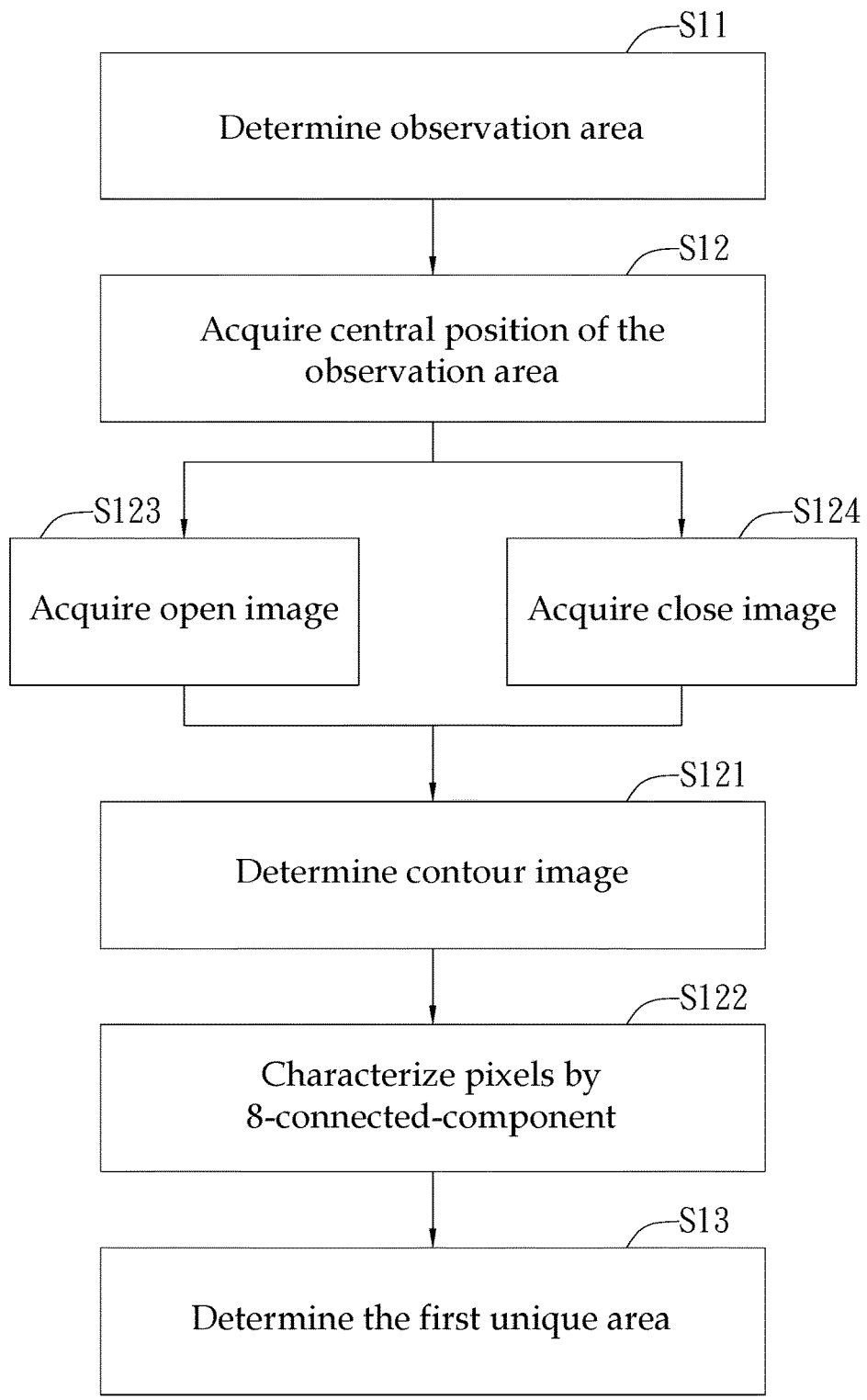
FIG. 5 is another flow chart of the image calibration method determine the first unique area of the present invention.

FIG. 5 is another flow chart of the process of determining the first unique area in the example of the image calibration method configured in the present invention. In an example of the present invention, the image calibration method can determine the contour image by an open or a close image. Please refer to FIG. 5, in the image calibration method of the example, after determining the observation area (Step S11) and acquiring the central position of the observation area (Step S12), the open image (Step 123) and close image (Step 124) of the first image frame can be acquired. The open and close image are methods of image processing in gradient morphology. The open image is the image which has been through the erosion then the dilation, and the close image is the image of the image frame which has been through the dilation then the erosion. By acquiring the absolute value of the difference between the open image and the close image, the image calibration method of the example can acquire the contour image (Step 121). Then, the pixel in the contour image is characterized by 8-connected-component (Step S122), so as to determine the first unique area in the contour image (Step S13).

On the other hand, in the detecting device and the configured image calibration method of the present invention, the gradient characteristic is related to the characteristic information of the gradient distribution and variation in the partial first image frame corresponded to the first unique area. More specifically, the image calibration method of the present invention can acquire the gradient characteristic of the partial first image frame corresponded to the first unique area by gray-level co-occurrence matrix (GLCM). In other words, by acquiring the Gray-Level Co-occurrence Matrix (GLCM) of the partial image frame corresponded to the first unique area, the image calibration method in the example of the present invention can find the partial image frame corresponded to the first unique area according to the GLCM in other image frames, and by calibrating the observation area according to the position variation of the first unique area, the detecting device can thus provide fine detecting function.

The detecting device and the configured image calibration method can also be used to calibrates the observation area by dividing the image frame into various sub-images. FIG. 6A to FIG. 6D are the schematic views of the image frame of the image calibration method in the second example of the present invention, wherein in order to explain explicitly the image calibration method of the example, the black or dark areas in the image frame are hatched, and the coloring parts are omitted in part of the schema so that each section in the image frame of the present invention can be indicated clearly, but this is not intended to limit the present invention.

Figure 6A:
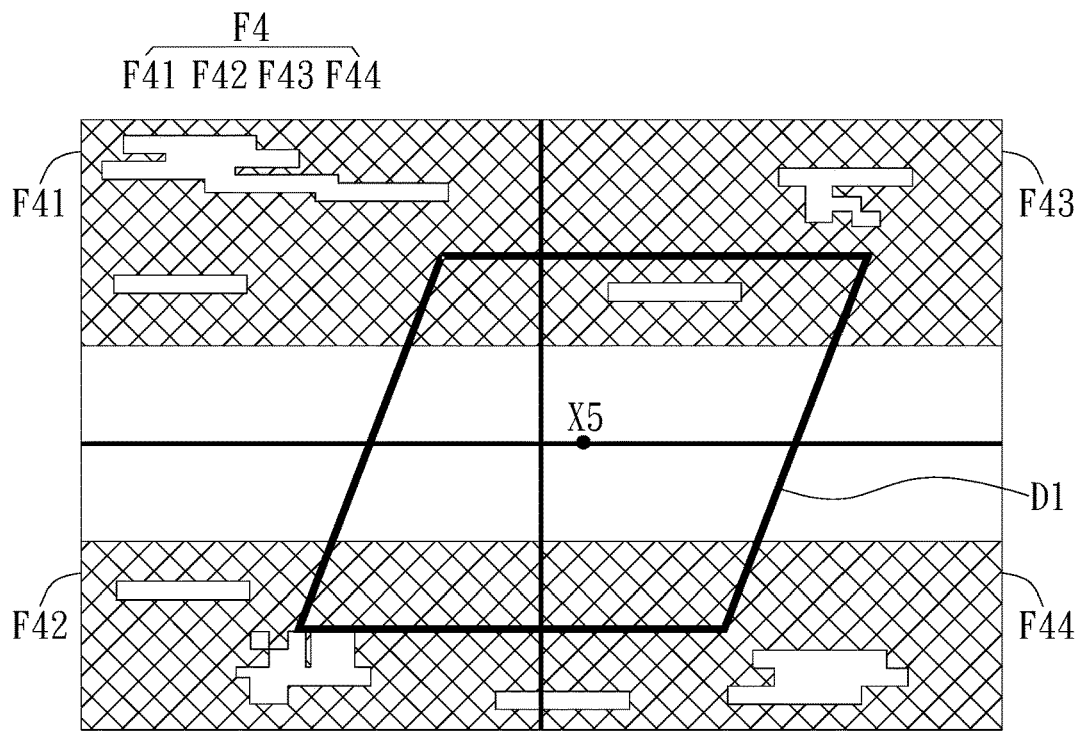
FIG. 6A to 6D are schematic views of the image frames during the image calibration method of the second embodiment of the present invention.
Figure 6B:
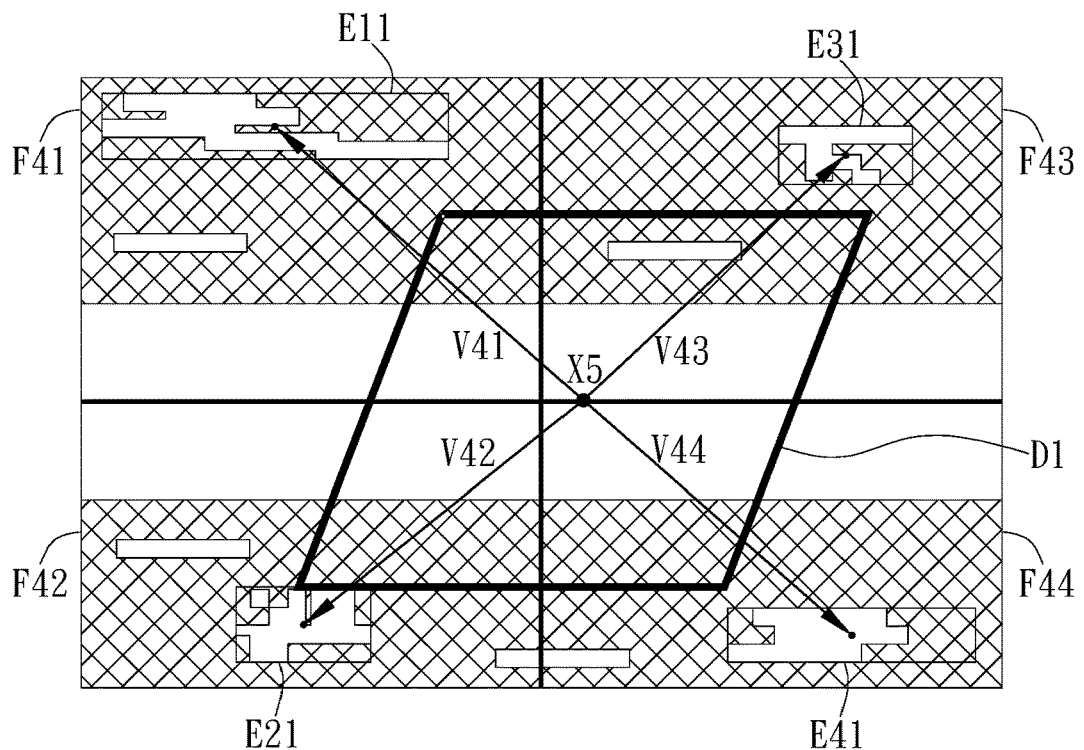

Please refer to FIG. 6A, in the image calibration method of the second example of the present invention, the image frame F4 is divided into various sub-images F41, F42, F43 and F44. To be more explicit, after the user determining the observation area D1 in the image frame F4 and acquiring the central position X5, the image calibration method of the example divides the image frame F4 into sub-image F41, F42, F43 and F44. Please refer to FIG. 6B, the image calibration method of the example acquires the unique area E11 in the sub-image F41, the unique area E21 in the sub-image F42, the unique area E31 in sub-image F43 and the unique area E41 in the sub-image F44. After acquiring the unique area E11, E21, E31 and E41, the image calibration method of the example determines the first vector V41, V42, V43 and V44 according to the central position X5 of the observation area D1, acquiring the gradient characteristic of the image frame in the unique area E11, E21, E31 and E41.

Specifically, in the second example of the present invention, the unique area E11, E21, E31 and E41 can be acquired by, for instance, the gradient morphology, determining these areas by contour image or 8-connected-component and finding the image in the image frame corresponded to these areas, then take the ray-level co-occurrence matrix (GLCM) of the images acquired in these parts as the gradient characteristic.

Figure 6C:
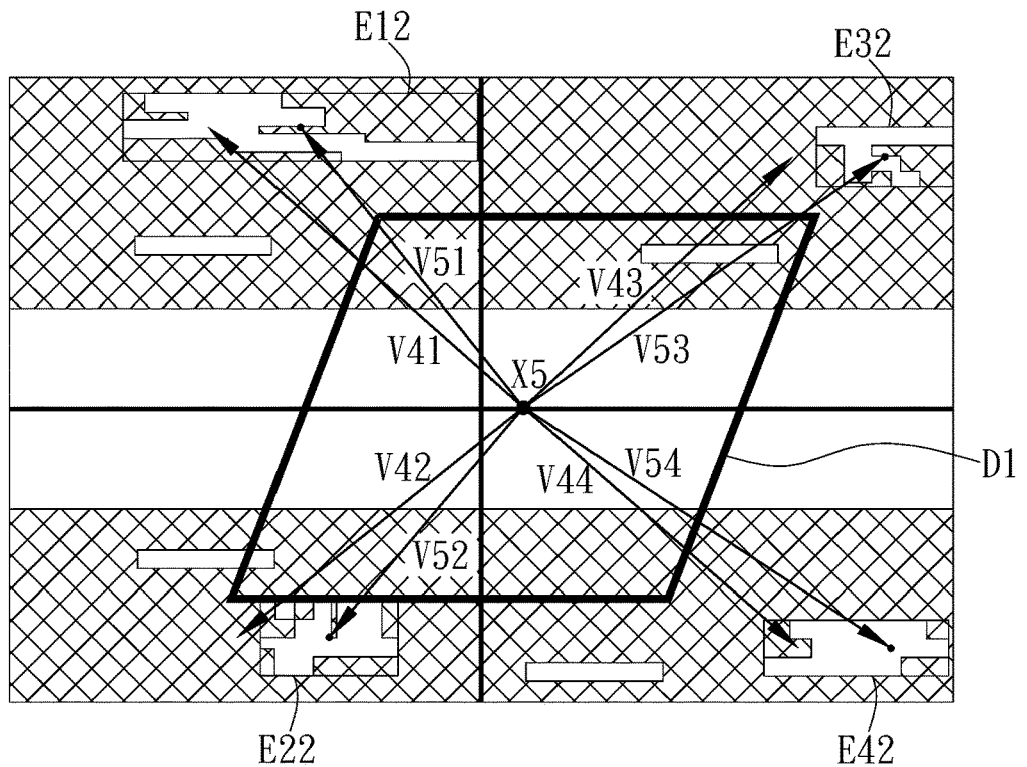

Please refer to FIG. 6C, in another image frame, the gradient characteristic finds respectively in the sub-images the second unique area E12, E22, E32 and E42. According to the central position X5 of the observation area A1, the second vectors V51, V52, V53 and V54 can be found in the image frame. In the example, each sub-image can characterize the calibration method of the observation area D1 according to the difference between the second and the first vector, wherein the difference between the second vector V51 and the first vector V41, the second vector V52 and the first vector V42, the second vector V53 and the first vector V43 as well as the second vector V54 and the first vector V44 can provide calibration vector to calibrate the observation area D1.

Figure 6D:
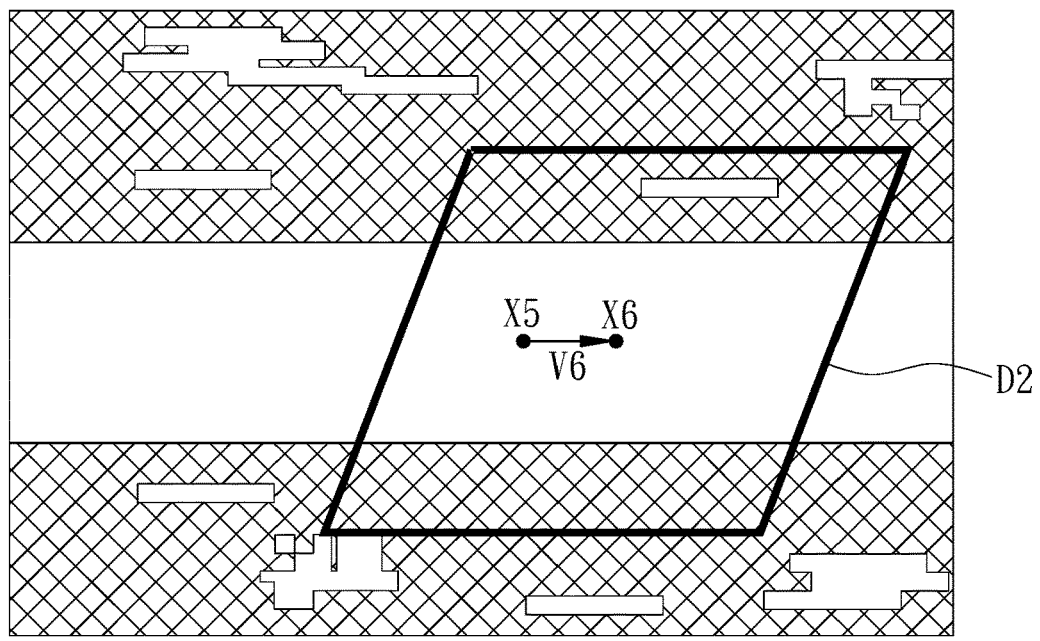

Please refer to FIG. 6D, by using the calibration vector V6 acquired from the difference between the second and the first vector, the image calibration method of the example can calibrate the central position X5 of the observation area D1 to central position X6, and also calibrate the observation area D1 to the observation area D2 so as to keep an appropriate observation position for providing fine detecting results.

Figure 7:
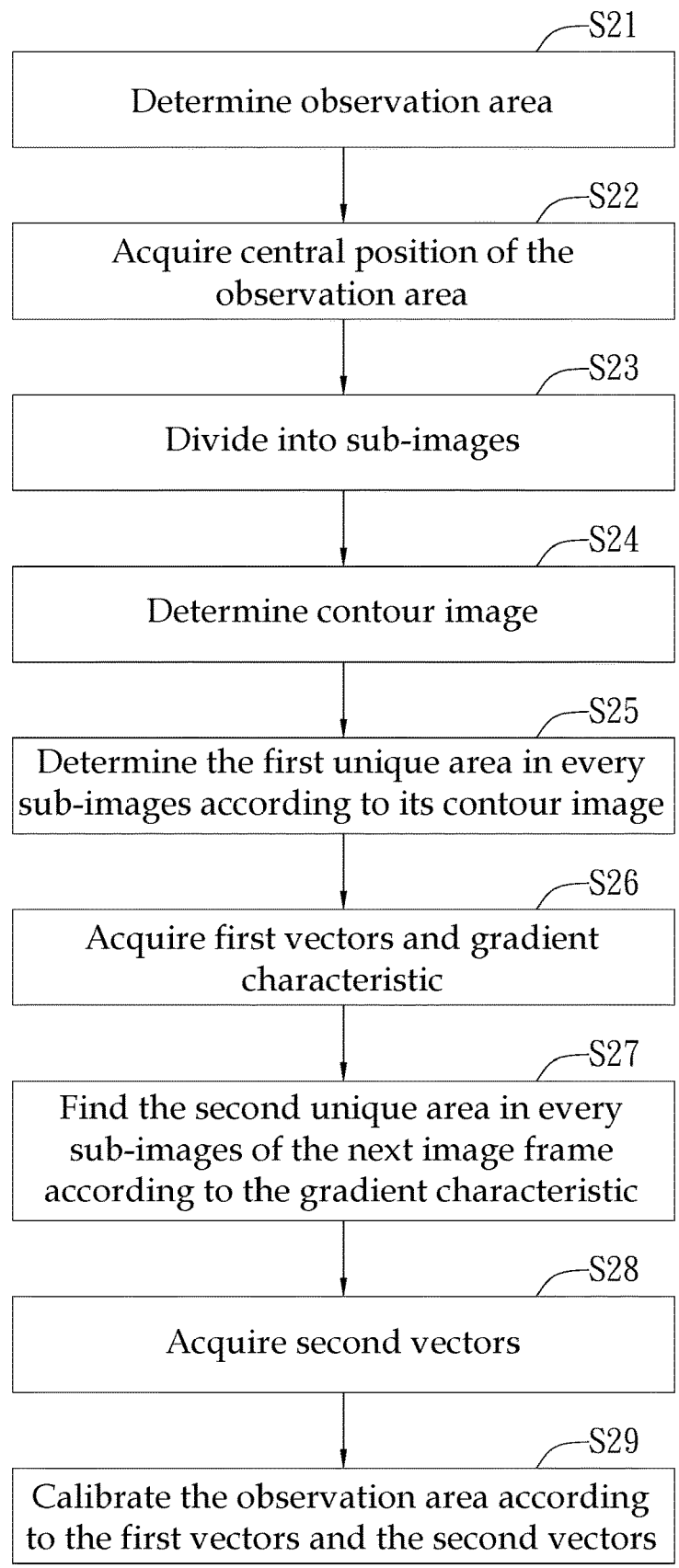
FIG. 7 is flow chart of the image calibration method of the second embodiment of the present invention.

FIG. 7 is the flow chart of the process of the image calibration method in the second example of the present invention. Please refer to FIG. 7, after the image calibration method of the example determining the observation area in the first image frame (Step S21), the central position of the observation area will be determined in the first image frame (Step S22). The first image frame will be divided into sub-images after acquiring the central position of the observation area (Step S23).

In the example, the first unique area can be acquired by a contour image. To be more explicit, after sub-image being divided, the image calibration method of the example acquires the contour image of the first image frame (Step S24) and determines the first unique area according to the contour image of each sub-image (Step S25). After acquiring these first unique areas, the first vectors are determined according to the positions of these first unique areas and the observation area, then, the gradient characteristics are acquired according to the partial sub-images corresponded to these first unique areas (Step S26) as the basis for calibrating the observation area later on.

After acquiring the next image frame as the second image frame, the image calibration method of the example finds the second unique area in each sub-image of the second image frame according to the gradient characteristic (Step S27), and determines the second vectors according to the second unique areas (Step S28). After acquiring the first and the second vectors, the observation area is calibrated based on the difference between these second and first vectors (Step S29) in order to keep the observation area in the image frame of the motion image at an appropriate position.

In conclusion, the image calibration method of the present invention can calibrate the position of the observation area in each image frame of the motion image. After the user determined the observation area in an image frame, the first vector can be acquire according to the position of the unique area and observation area in the image frame; then the user can find the unique area in other image frames and calibrate the position of the observation area in other image frames according to the position of the unique area in other image frames so as to provide a image calibration method. With the unique area and its gradient characteristic, the detecting device of the present invention can keep the observation area at an appropriate position in every image frame so as to provide a fine detecting function.

The invention claimed is:

1. An image calibration method for calibrating position of an observation area in a motion image, the motion image comprising a plurality of image frames, the method comprising:
   determining the observation area of the motion image in a first image frame of the motion image and acquiring a central position of the observation area of the motion image;
   determining a first unique area in the first image frame, and the first unique area complying a gradient characteristic, wherein the gradient characteristic is that the first unique area has a greater variation of gradient intensity than a variation of the gradient intensity in other part of the first image frame;
   acquiring a first vector pointing from the central position of the observation area to a central position of the first unique area in the first image frame;
   determining a second unique area in a second image frame of the motion image according to the gradient characteristic;
   acquiring a second vector pointing from the central position of the observation area to a central position of the second unique area in the second image frame; and
   calibrating position of the observation area in a third image frame according to a difference between the first vector and the second vector.

2. The image calibration method of claim 1, the step of determining the first unique area of the motion image comprising: determining a contour image of the first image frame; determining the first unique area from the contour image, wherein pixels of a part of the contour image in the first unique area containing the same connected-component labeling; and acquiring the gradient characteristic from a part of the first image frame corresponding to the first unique area.

3. The image calibration method of claim 2, the step of determining the contour image comprising:
   acquiring an open image and a close image of the first image frame, wherein the open image is the first image frame which has been through erosion and then dilation of morphology in digital image processing techniques, and the close image is the first image frame which has been through the dilation then the erosion; and
   determining the contour image with an absolute value of a difference between the open image and the close image.

4. The image calibration method of claim 2, the step of determining the first unique area comprising:
   dividing the contour image into various pixel groups according to a connected-component method; and determining a pixel group with a largest number of pixels among the pixel groups as the first unique area.

5. The image calibration method of claim 2, the method for acquiring the gradient characteristic further comprising: determining a gray-level co-occurrence matrix (GLCM) of the partial first image frame corresponded to the first unique area as the gradient characteristic.

6. The image calibration method of claim 1, the step of determining the first unique area further comprising: dividing the first image frame into various sub-images; and determining the first unique area in each sub-image; wherein the step of finding the second unique area in the second image frame according to the gradient characteristic further comprises: dividing the second image frame into various sub-images according to the sub-images divided from the first image frame; and finding the second unique area in each sub-image of the second image frame according to the gradient characteristics.

7. The image calibration method of claim 1, wherein the motion image is ultrasound image, after the user determining the observation area in the first image frame of the motion image further comprising: acquiring the corresponding Doppler signal of partial image frames in the observation area.

8. A detecting device comprising: an image capturing device for capturing a motion image, the motion image having a plurality of image frames from an organism; a processor connecting to the image capturing device, and acquiring the motion image from the image capturing device; a displayer connecting to the processor, and displaying the motion image; and an input device connecting to the processor, and determining an observation area of the motion image in a first image frame of the motion image; wherein the processor acquires a central position of the observation area after determining the observation area of the motion image, and determines a first unique area in the first image frame complying with a gradient characteristic, wherein the gradient characteristic is that the first unique area has a greater variation of gradient intensity than a variation of the gradient intensity in other part of the first image frame, acquires a first vector pointing from the central position of the observation area to a central position of the first unique area, determines a second unique area in a second image frame of the motion image according to the gradient characteristic, acquires a second vector pointing from the central position of the observation area to a central position of the second unique area in the second image frame, and calibrates the observation area in a third image frame according to a difference between the first vector and the second vector, and the displayer displays the third image.

9. The detecting device of claim 8, wherein the processor determines a contour image of the first image frame; at least the first unique area is determined from the contour image, wherein pixels of a part of the contour image in the first unique area contains the same connected-component labeling; the processor acquires the gradient characteristic from a part of the first image frame corresponding to the first unique area.

10. The detecting device of claim 9, wherein the processor acquires an open image and a close image of the first image frame; wherein the open image is the first image frame which has been through erosion then dilation of morphology in digital image processing techniques, and the close image is the first image frame which has been through the dilation then the erosion; and an absolute value of a difference between the open image and the close image determines the contour image.

11. The detecting device of claim 9, wherein the processor divides the contour into various pixel groups according to connected-component and determines a pixel group with the largest number of pixels among the pixel groups as the first unique area.

12. The detecting device of claim 9, wherein the processor divides contour into various sub-images and determines the first unique area in each sub-image;
when the processor searches for the second unique area in the second image frame, the second image frame is divided into various sub-images according to the sub-images of the first image frame; and the processor finds the second unique area in each sub-image of the second image frame according to the gradient characteristic.

13. The detecting device of claim 9, wherein the processor determines the gray-level co-occurrence matrix (GLCM) of the partial first image frame corresponded to the first unique area as the gradient characteristic.

14. The detecting device of claim 8, the image capturing device comprising an ultrasound probe; after the user determining the observation area in the first image frame of the motion image, the processor acquires the corresponding Doppler signal of the partial image frame in the observation area from the ultrasound probe.

* * * * *